(12) United States Patent
Kapre et al.

(10) Patent No.: US 11,366,458 B2
(45) Date of Patent: Jun. 21, 2022

(54) JUST-IN-TIME BIOPROCESS PLANT SYSTEM

(71) Applicant: Inventprise, LLC, Redmond, WA (US)

(72) Inventors: Subhash V. Kapre, Redmond, WA (US); Kapil S. Kapre, Redmond, WA (US)

(73) Assignee: Inventprise, LLC, Redmond, WA (US)

( * ) Notice: Subject to any disclaimer, the term of this patent is extended or adjusted under 35 U.S.C. 154(b) by 124 days.

(21) Appl. No.: 16/686,337

(22) Filed: Nov. 18, 2019

(65) Prior Publication Data

US 2020/0159198 A1    May 21, 2020

Related U.S. Application Data

(60) Provisional application No. 62/768,875, filed on Nov. 17, 2018.

(51) Int. Cl.
G05B 19/418 (2006.01)
G06F 16/901 (2019.01)
G16H 50/20 (2018.01)
G06F 13/40 (2006.01)

(52) U.S. Cl.
CPC ... *G05B 19/41885* (2013.01); *G05B 19/4183* (2013.01); *G05B 19/4184* (2013.01); *G06F 13/4081* (2013.01); *G06F 16/901* (2019.01); *G16H 50/20* (2018.01)

(58) Field of Classification Search
None
See application file for complete search history.

(56) References Cited

U.S. PATENT DOCUMENTS

| 2005/0226794 | A1 | 10/2005 | Hodge et al. |
| 2014/0097700 | A1 | 4/2014 | Law et al. |
| 2015/0064768 | A1 | 3/2015 | Kapre |
| 2015/0175950 | A1 | 6/2015 | Hirschel et al. |

FOREIGN PATENT DOCUMENTS

WO    WO 97/07443    2/1997

OTHER PUBLICATIONS

Gonzales Rodriguez, Sergio, "Current Developments in Biotechnology and Bioengineering", Elsevier 2017 (Year: 2017).*
PCT Search Report and Written Opinion for PCT/US19/61918, dated Feb. 2, 2020.
Office Action for Indian Pat. App. No. 202117023032 dated Mar. 3, 2022.

* cited by examiner

*Primary Examiner* — Carlos R Ortiz Rodriguez
(74) *Attorney, Agent, or Firm* — Remenick PLLC

(57) ABSTRACT

An integrated platform system controlled with hardware and software for just-in-time, local manufacturing is disclosed. System hardware may include a fermentation system, a cross-flow system, a disposable formulation system, a robotic fill-finish system, and a quality control test and release system.

16 Claims, 5 Drawing Sheets

US 11,366,458 B2

JUST-IN-TIME BIOPROCESS PLANT SYSTEM

REFERENCE TO RELATED APPLICATIONS

The present application claims priority to Provisional U.S. Application No. 62/768,875, filed Nov. 17, 2018, entitled "JUST-IN-TIME BIOPROCESS PLANT SYSTEM," and is incorporated herein in its entirety.

BACKGROUND

1. Field of the Invention

The invention is directed to systems and methods of controlling bioprocess plants, more specifically, the invention is directed to systems and methods of Just-In-Time (JIT) solutions to address the manufacturing needs for small scale bioprocess plan operations.

2. Background of the Invention

Manufacturing of vaccines and other biologicals typically requires continuous production using a pathogenic organism. The manufactured biologicals often need to be stockpiled, for example for use against a biothreat, at great cost to a government or private entity. Furthermore, the biologicals are often stored at locations far from where they are needed adding distribution, transportation, support, and logistics costs and time. Transporting over international boarders may also add challenges. For example, at the location of distribution, there may not be sufficient trained manpower, there may be a lack of infrastructure, support, and technology transfer mechanisms. The cost of quality assurance and quality control could be expensive at the point of distribution.

Therefore, there is a need for a system for manufacturing biologicals on or near location on a just-in-time (JIT) basis. There is also a need for manufacturing small quantities of biologicals at costs similar to mass production manufacturing.

SUMMARY OF THE INVENTION

The present invention overcomes the problems and disadvantages associated with current strategies and designs and provides low cost, JIT manufacturing of biologicals.

Other embodiments and advantages of the invention are set forth in part in the description, which follows, and in part, may be obvious from this description, or may be learned from the practice of the invention.

DESCRIPTION OF THE DRAWING

The invention is described in greater detail by way of example only and with reference to the attached drawing, in which.

DESCRIPTION OF THE INVENTION

Figure 1:
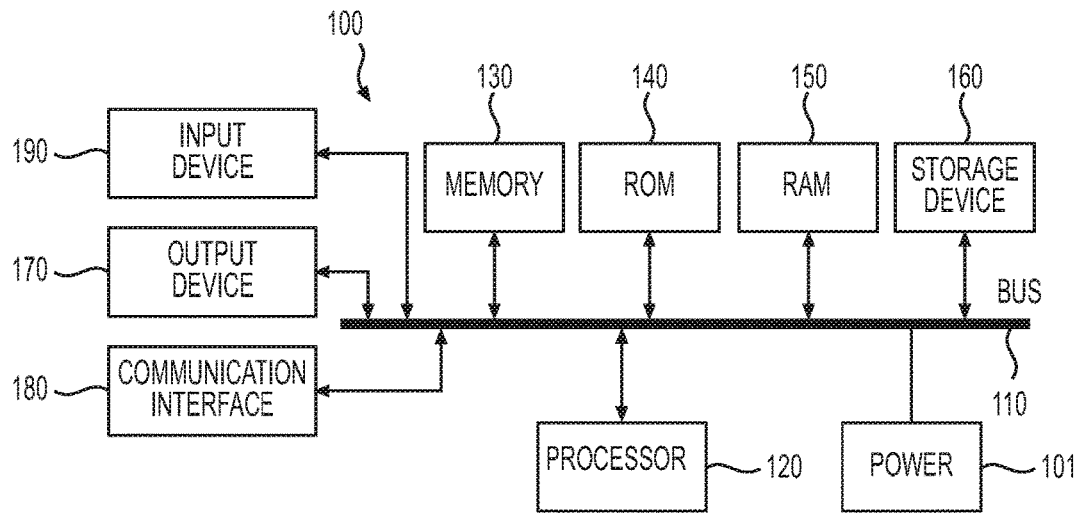
FIG. 1 depicts an embodiment of a computing system.

As embodied and broadly described herein, the disclosures herein provide detailed embodiments of the invention. However, the disclosed embodiments are merely exemplary of the invention that may be embodied in various and alternative forms. Therefore, there is no intent that specific structural and functional details should be limiting, but rather the intention is that they provide a basis for the claims and as a representative basis for teaching one skilled in the art to variously employ the present invention FIG. 1 depicts a schematic of a preferred embodiment of a computing device 100. Device 100 preferably includes a power source 101. For example, power source 101 may be a battery, a chemical power source, a solar energy converter, a power converter to receive power from a wall receptacle or the like, a mechanical power source, or source of power.

Power source 101 is preferably used to supply power to the remaining components of computing device 100. Computing device 100 preferably further includes an integrated circuit (i.e. a system on a chip (SoC)). The SoC preferably integrates multiple components of a computer or other electronic system into a single chip. It may contain digital, analog, mixed-signal, and radio-frequency functions all on a single chip substrate. The SoC preferably incorporates one or more of a central processing unit (CPU), a graphics processing unit (GPU), and a system bus 1 that couples various system components including the system memory 130, dynamic random access memory (RAM) 150 and flash memory 160, to the SoC. The system bus may be one of several types of bus structures including a memory bus or memory controller, a peripheral bus, or a local bus using one of a variety of bus architectures. A basic input/output (BIOS) stored in flash memory 160 or the like, may provide the basic routine that helps to transfer information between elements within computing device 100, such as during start-up. The drives and the associated computer readable media provide nonvolatile storage of computer readable instructions, data structures, program modules and other data for computing device 500. The basic components are known to those of skill in the art and appropriate variations are contemplated.

Although the exemplary environment described herein employs flash memory, it is appreciated by those skilled in the art that other types of computer readable media which can store data that are accessible by a computer, such as magnetic cassettes, hard drives, digital versatile disks, cartridges, random access memories (RAMs) 150, read only memory (ROM) 140, a cable or wireless signal containing a bit stream and the like, may also be used in the exemplary operating environment.

Computing device 100 further preferably includes a networking device 180. Networking device 180 is able to connect to, for example, the Internet, one or more Local Area Networks ("LANs"), one or more Metropolitan Area Networks ("MANs"), one or more Wide Area Networks ("WANs"), one or more Intranets, etc. Networking device 180 may be capable of connecting to wireless Bluetooth devices (e.g. a keyboard or a mouse). Preferably, networking device 180 is a wireless networking device (e.g. Wi-Fi), however hard-wired networks can be coupled to networking device 180 (e.g. ethernet). Furthermore, networking device 180 may also connect to distributed computing environments where tasks are performed by local and remote processing devices that are linked (either by hardwired links, wireless links, or by a combination thereof) through a communications network. In a distributed computing environment, program modules may be located in both local and remote memory storage devices.

To enable user interaction with computing device 100, there is preferably an input receiving device 190. Input receiving device 190 can receive input from a number of input mechanisms, such as a microphone for speech, a touch-sensitive screen for gesture or graphical input, a keyboard, a mouse, motion input, RJ-45, USB, and so forth. In some instances, multimodal systems enable a user to provide multiple types of input to communicate with the computing device 100. There is no restriction on the invention operating on any particular hardware arrangement and therefore the basic features here may easily be substituted for improved hardware or firmware arrangements as they are developed.

Computing device 100 further preferably includes at least one output port 170. Output port 170 connects computing device 100 to a TV, speaker, projector, or other audio-visual device. Preferably, output port 170 is a HDMI port, optical audio port, serial port, USB port, networking port, s-video port, coaxial cable port, composite video, composite audio, and/or VGA port. In preferred embodiments, computing device 100 may also include additional auxiliary components (e.g. power management devices or digital audio convertors).

For clarity of explanation, the illustrative system embodiments are presented as comprising individual functional blocks. The functions these blocks represent may be provided through the use of either shared or dedicated hardware, including, but not limited to, hardware capable of executing software. For example, the functions of one or more processors presented in FIG. 1 may be provided by a single shared processor or multiple processors. (Use of the term "processor" should not be construed to refer exclusively to hardware capable of executing software.) Illustrative embodiments may comprise microprocessor and/or digital signal processor (DSP) hardware, read-only memory (ROM) for storing software performing the operations discussed below, and random access memory (RAM) for storing results. Very large-scale integration (VLSI) hardware embodiments, as well as custom VLSI circuitry in combination with a general purpose DSP circuit, may also be provided.

Embodiments within the scope of the present invention include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a computer, specialty computer, or special purpose processing device to perform a certain function or group of functions. Computer-executable instructions also include program modules that are executed by computers in stand-alone or network environments. Generally, program modules include routines, programs, objects, components, and data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Figure 2:
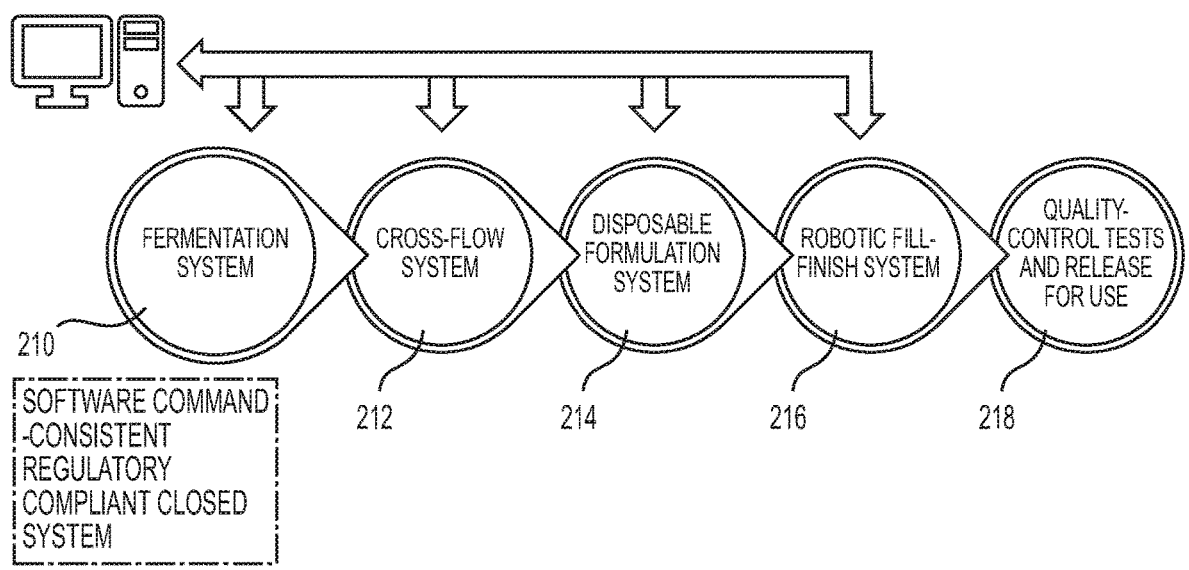
FIG. 2 depicts an embodiment of system hardware.

Preferably, the system is an integrated platform system controlled with hardware and software for JIT, local manufacturing. As shown in FIG. 2, system hardware may include a fermentation system 210, a cross-flow system 212, a disposable formulation system 214, a robotic fill-finish system 216, and a quality control test and release system 218.

Figure 3:
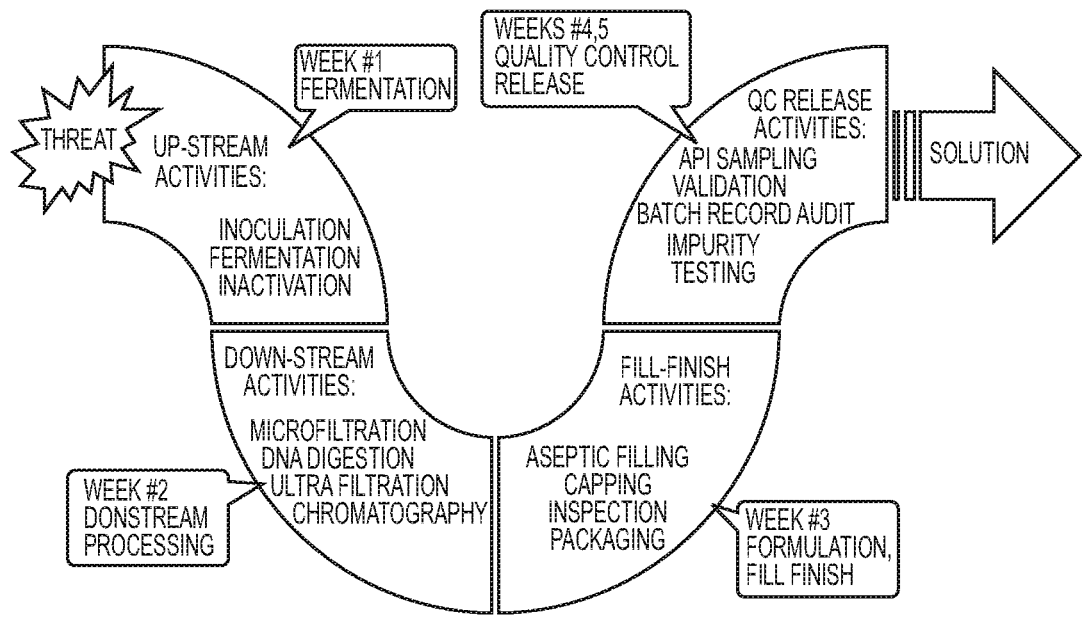
FIG. 3 depicts an embodiment of a timeline for manufacturing a vaccine.

The system preferably addresses the need for prompt manufacturing of biologicals, for example a Yellow Fever Vaccine. The software command system preferably guides the processes as a closed system with regulatory compliance. FIG. 3 depicts an embodiment of a timeline of the manufacturing process. Once the threat is detected, fermentation starts at Week #1. The Week #1 up-stream activities preferably include inoculation, fermentation, and inactivation. Downstream processing preferably starts at Week #2. The Week #2 downstream activities preferably include microfiltration, DNA digestion, ultra-filtration, and chromatography. Formulation and fill-finish activities begin at Week #3. Week #3 activities preferably include aseptic filling, capping, inspection, and packaging. At Weeks #4 and 5 the solution is released form quality control. Quality control activities preferably include API sampling, validation, batch record audit, and impurity testing. The process may take one, two, three or less weeks from the mini bioreactor through the downstream processing system. Preferably, the system works with minimal human involvement, and through 24×7 operation. Thereby providing substantial saving in cost and time. Preferably, the system avoids need to stockpile. The plant can preferably be designed at a scale that would avoid any storage need. The formulation and fill-finish preferably takes one, two, three, or less week with robotic integration. Quality control release preferably takes one, two, three, or less weeks with standardized specifications. The total time for the process preferably is two, three, four, five, five and a half, six, or less weeks. Preferably, the system provides horizontal and vertical scalability with centralized and remote capabilities.

Preferably, the system has integrated hardware, where various steps in a bioprocess are linked in one system. Given a process, the central CPU/command module preferably controls the hardware, with appropriate checks and balances using a master formula, resulting in a continuous and robust operation, through a proprietary integrated hardware-software solution. A second software solution preferably documents the process, creating a tamper-proof BMR (Batch Manufacturing Records) database. Preferably, the system is CFR 21 compliant. The system may include CIP (clean in place) and SIP (sterilize in place) steps. Preferably, the process works without human intervention, saving time and minimization of costs with ease in remote placement.

The system hardware can preferably scale vertically from the smaller end at 100 L or below and upwards to 1000 L or beyond. With no-stockpiling as a pre-requisite, the actual volume is preferably tied to the required yield of the specific process. The software platform is preferably scale-agnostic. The integrated hardware-software platform preferably addresses horizontal scaling via a plug-and-play approach, a way of discretizing a process into unit operations. Horizontal scaling preferably allows for manufacturing different solutions to a variety of current and emerging threats while being validated in a controlled execution. The plug-and-play system also allows for increasing production as required to meet demand in a tamper-proof validated platform. The platform's ability to scale may have a minimum and/or a maximum. This vertical (e.g. amount of production) and horizontal (e.g type of production) scalability preferably allows the platform to address localized production in the field (needs of countermeasure solutions). The tight integration preferably reduces the footprint of the process system drastically, and human intervention is highly minimized. The process preferably operates using an authorized 'recipe of steps' as an essentially closed system, isolating the product, environment, and personnel. Preferably, the system compiles with FDA Regulations under Title 21, Part 11. There may be a unique tamper-proof electronic record system with biometric security. The plant is preferably self-cleaning and self-sterilizing.

The system preferably operates, records and documents, the various operations for Current Good Manufacturing Practices (cGMP) compliance. All product contact parts are preferably Current Good Manufacturing Practices (cGMP) certified. The solution is preferably CFR 21 compliant. Quality assurance (QA) preferably has oversight over the system and the live-process, also the master-formula is preferably informed by QA recommendations. QA preferably has control over actions taken when deviations occur. Deviations, and associated corrective actions if any, are preferably documented.

The Platform components from the mini bioreactor to the down-stream system are preferably designed to follow identical operation of process parameters at all levels of operating scale. The process, after validation, may work anywhere to produce licensed products (using licensed clones), if identical process system is used. Due to its compactness, the plant is preferably highly mobile and can work in conditions where human capital/resources are limited. Due to a closed system operation, controlled milieu (e.g. air, water requirements) are preferably minimal. Since the Platform can work 24×7, it is preferably a high throughput system, both operationally (i.e. running factory) and technically, and a certain horizontal and/or vertical scalability is possible. Since cleaning and sterilizing process are automatic, human intervention is preferably minimal, lowering costs further.

Figure 4:
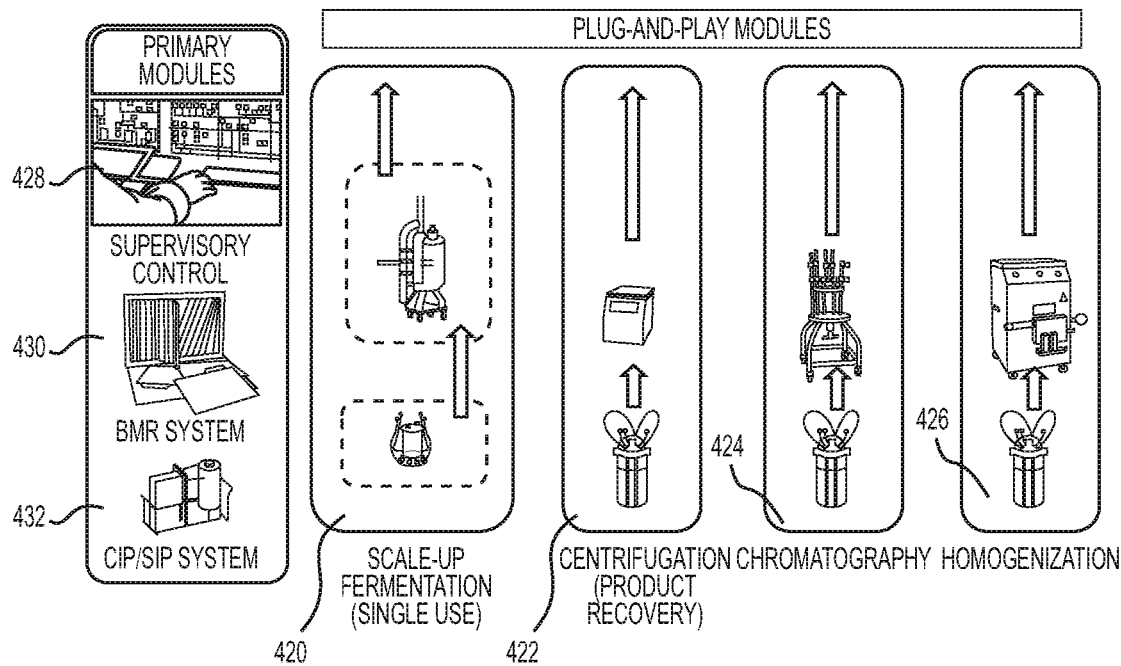
FIG. 4 depicts embodiments of plug-and-play modules.
Figure 5:
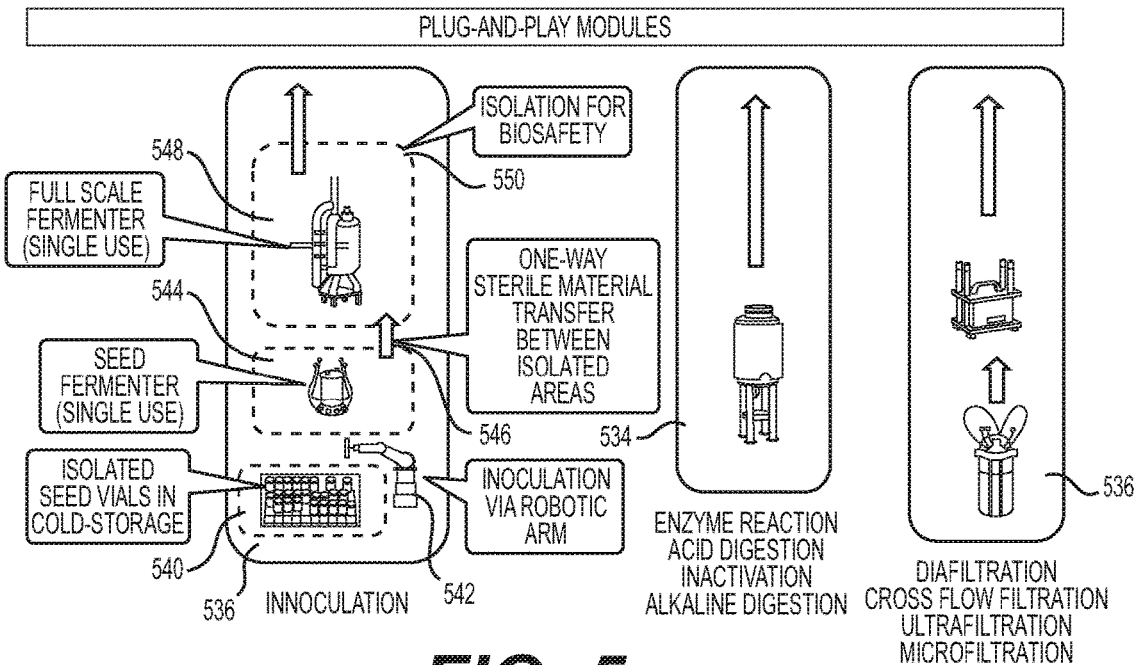
FIG. 5 depicts additional embodiments of plug-and-play modules.

A Bioprocess plant may be an embodiment of the plug-and-play platform system. The plant is preferably a downstream process plant that integrates with an upstream process. The plant is preferably consistent and a closed system. The plant preferably allows for easy regulatory compliance, ease in deployment due to its small footprint, and horizontal scalability via unit operations. As shown in FIG. 4, Plug-and-play modules may include scale-up fermentation 420, centrifugation 422, chromatography 424, and homogenization 426. Other modules (shown in FIG. 5) may include enzyme reaction, acid digestion, inactivation, alkaline digestion 534, diafiltration, cross flow filtration, ultrafiltration, microfiltration 536, and inoculation 538. The inoculation 538 module may include isolated seed vials in cold-storage 540, a robotic arm 542 for inoculation, a seed fermenter 544 (single or multiple use), a one-way sterile material transfer system 546 for transferring between isolated areas, a full scale fermenter 548 (single or multiple use), and an isolation system 550 for biosafety. Primary Modules (shown in FIG. 4) may include supervisory control 428, BMR system 430, and CIP/SIP system 432. Preferably the supervisory control 428 is able to detect which modules are included in the system and how to control the flow of matter through each module to manufacture the desired solution. The plant may be used for manufacturing polysaccharide vaccines, inactivated whole-cell pertussis vaccines, cell based inactivated influenza vaccines, inactivated rabies vaccines, hepatitis vaccines, and yellow fever live-attenuated vaccines.

Preferably, the system addresses the issues challenging anti-biothreat production today including the need for stockpiling (the platform preferably reduces the need and quantity due to JIT production, being both horizontally and vertically scalable), distribution challenges (the platform is preferably able to produce centrally and "in the field" with relieve pressure on logistics to move product where needed, in case of multi-site biothreat outbreaks), and international concerns.

Preferably, the system can create process step modules and can join them depending on the process. The developed software preferably drives the process flow to achieve purification. Each Bio Process may need different steps. Since the system is modular, components may be joined as needed based on the product to be manufactured and the system preferably can use a common software to purify. The system preferably creates a seamless process pathway without the need to break process steps. Plus a second software is preferably able to record information to form a running batch manufacturing record. The system preferably will alert the quality assurance department if there is any breakdown in the process and transmit instruction to make an acceptable deviation in case of any change.

Preferably, the platform technology is capable of handling cells, viruses, bacteria, bacterial products, recombinant products, vectored products. Preferably, the system is capable of making vaccines in remote areas. Common support systems can preferably oversee the establishment and prevent failures. Due to uniform efficiency cost of the bulk vaccine would preferably be controlled to give the same benefits as a large plant.

The following examples illustrate embodiments of the invention, but should not be viewed as limiting the scope of the invention.

Examples

Figure 6:
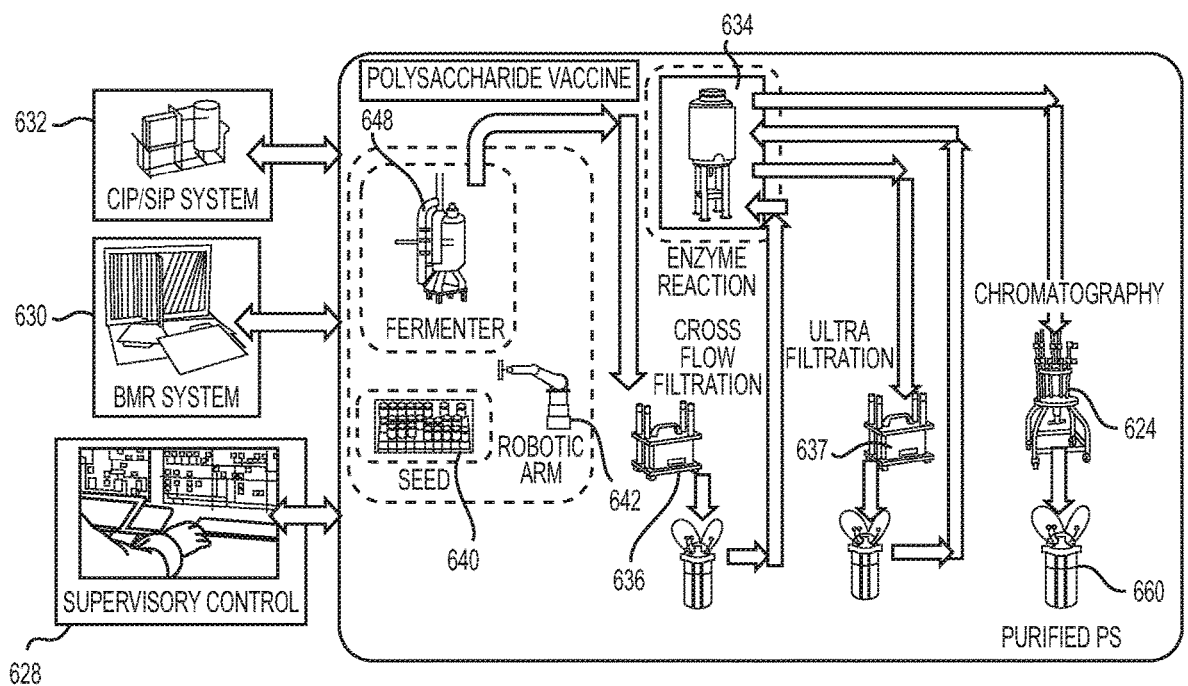
FIG. 6 depicts an embodiment of a polysaccharide vaccine manufacturing system.

Example 1 A Platform Solution for Manufacturing Polysaccharide Vaccines on a Small Scale FIG. 6 depicts an embodiment of a system for manufacturing polysaccharide vaccines. The system includes supervisory control 628 adapted to autonomously control all of the modules of the system. BMR system 630 preferably stores the "recipe" for manufacturing the vaccine. Preferably, supervisory control 628 accesses data from BMR system 630 to control the remaining modules to manufacture the vaccine. CIP/SIP system 632 maintains the sterility of the system.

The plug-and-play modules for manufacturing a polysaccharide vaccine preferably include seeds 640, inoculation robotic arm 642, fermenter 648, cross-flow filtration system 636, enzyme reactor 634, ultra-filtration system 637, and chromatography 624. The supervisory control 628 preferably controls the flow of material through the modules to manufacture the purified polysaccharide (PS) vaccine 660. As shown in the figure, filtration may occur multiple times during the process.

Figure 7:
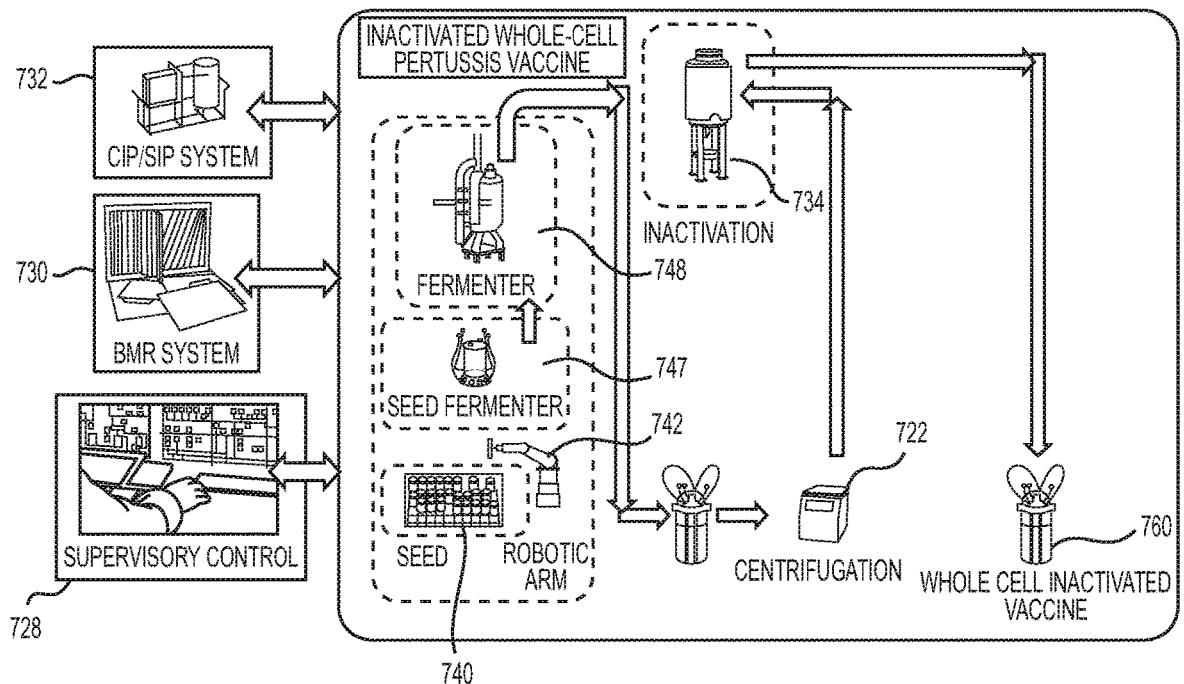
FIG. 7 depicts an embodiment of an inactivated whole-cell pertussis vaccine manufacturing system.

Example 2 A Platform Solution for Manufacturing Inactivated Whole-Cell Pertussis Vaccine on a Small Scale FIG. 7 depicts an embodiment of a system for manufacturing inactivated whole-cell pertussis vaccines. The system includes supervisory control 728 adapted to autonomously control all of the modules of the system. BMR system 730 preferably stores the "recipe" for manufacturing the vaccine. Preferably, supervisory control 728 accesses data from BMR system 730 to control the remaining modules to manufacture the vaccine. CIP/SIP system 732 maintains the sterility of the system.

The plug-and-play modules for manufacturing an inactivated whole-cell pertussis vaccine preferably include seeds 740, inoculation robotic arm 742, seed fermenter 747, fermenter 748, centrifuge 722, and inactivation system 734. The supervisory control 728 preferably controls the flow of material through the modules to manufacture the whole-cell inactivated vaccine 760.

Figure 8:
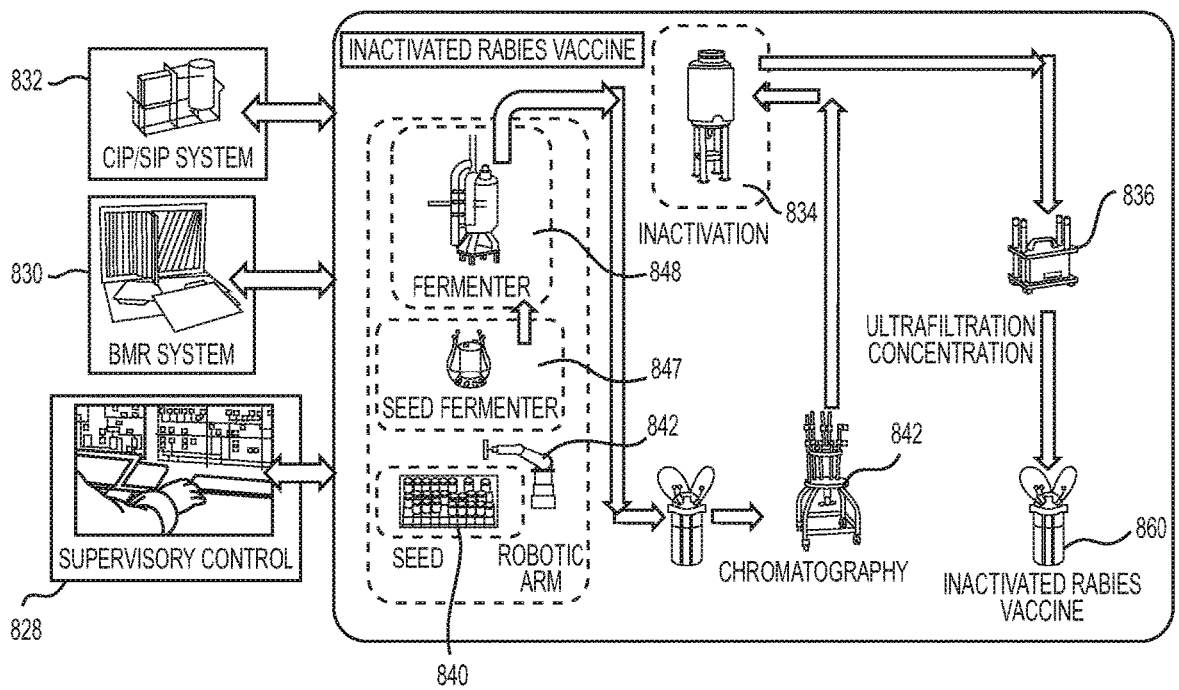
FIG. 8 depicts an embodiment of an inactivated rabies vaccine manufacturing system.

Example 3 A Platform Solution for Manufacturing Inactivated Rabies Vaccine on a Small Scale FIG. 8 depicts an embodiment of a system for manufacturing inactivated rabies vaccines. The system includes supervisory control 828 adapted to autonomously control all of the modules of the system. BMR system 830 preferably stores the "recipe" for manufacturing the vaccine. Preferably, supervisory control 828 accesses data from BMR system 830 to control the remaining modules to manufacture the vaccine. CIP/SIP system 832 maintains the sterility of the system.

The plug-and-play modules for manufacturing a rabies vaccine preferably include seeds 840, inoculation robotic arm 842, seed fermenter 847, fermenter 848, inactivation system 834, chromatography 842, and ultra-filtration concentration system 836. The supervisory control 828 preferably controls the flow of material through the modules to manufacture the rabies vaccine 860.

Figure 9:
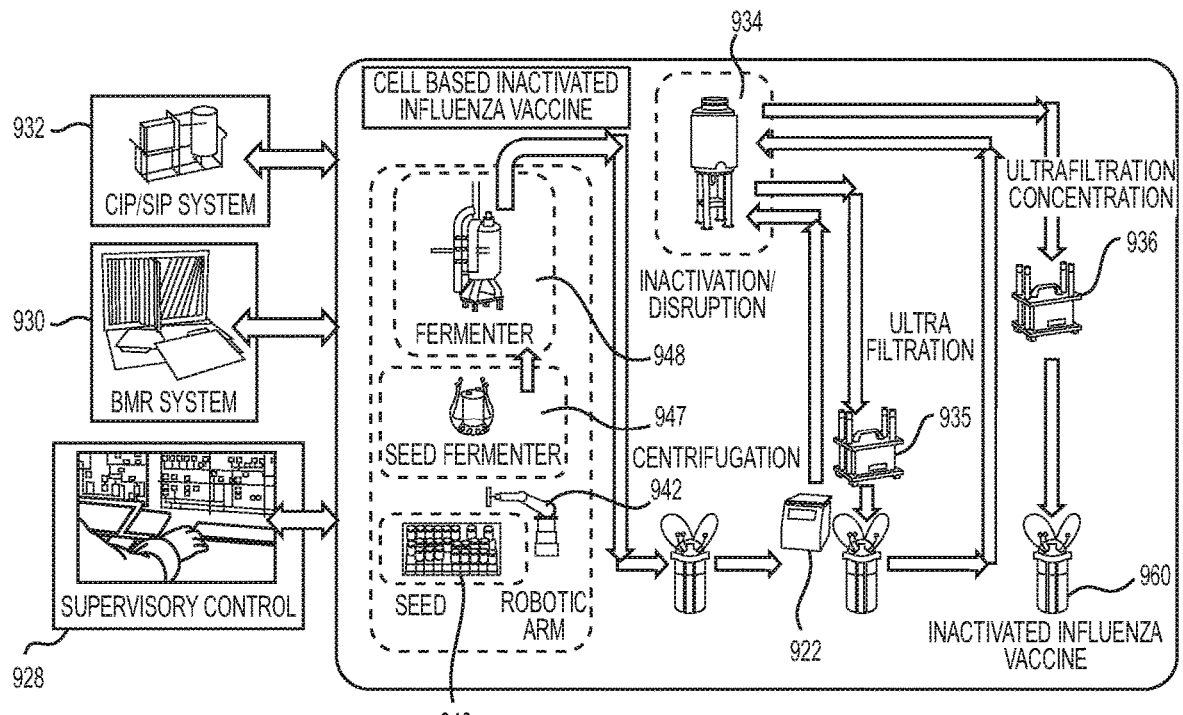
FIG. 9 depicts an embodiment of a cell based inactivated influenza vaccine manufacturing system.

Example 4 A Platform Solution for Manufacturing Cell Based Inactivated Influenza Vaccine on a Small Scale FIG. 9 depicts an embodiment of a system for manufacturing cell based inactivated influenza vaccines. The system includes supervisory control 928 adapted to autonomously control all of the modules of the system. BMR system 930 preferably stores the "recipe" for manufacturing the vaccine. Preferably, supervisory control 928 accesses data from BMR system 930 to control the remaining modules to manufacture the vaccine. CIP/SIP system 932 maintains the sterility of the system.

The plug-and-play modules for manufacturing an influenza vaccine preferably include seeds 940, inoculation robotic arm 942, seed fermenter 947, fermenter 948, centrifuge 922, inactivation/disruption system 934, ultra-filtration system 935, and ultra-filtration concentration system 936. The supervisory control 928 preferably controls the flow of material through the modules to manufacture the influenza vaccine 960.

Figure 10:
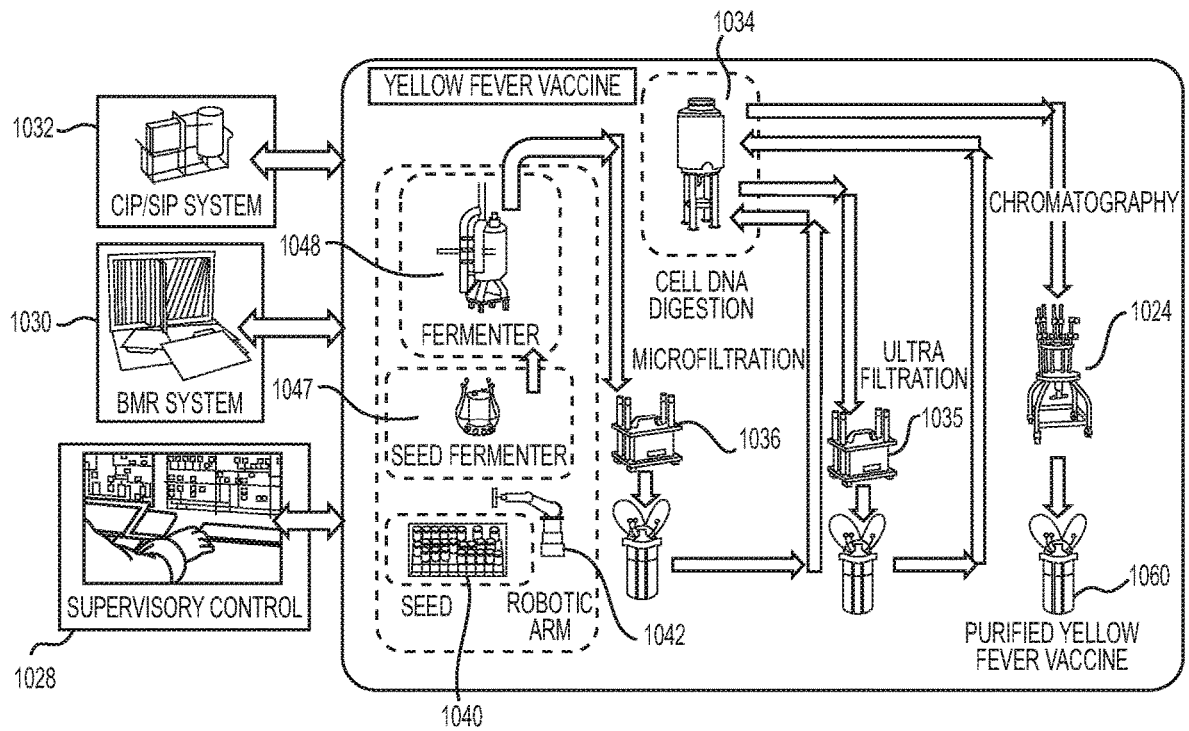
FIG. 10 depicts an embodiment of a yellow fever vaccine manufacturing system.

Example 5 A Platform Solution for Manufacturing Yellow Fever Vaccine on a Small Scale FIG. 10 depicts an embodiment of a system for manufacturing yellow fever vaccines. The system includes supervisory control 1028 adapted to autonomously control all of the modules of the system. BMR system 1030 preferably stores the "recipe" for manufacturing the vaccine. Preferably, supervisory control 1028 accesses data from BMR system 1030 to control the remaining modules to manufacture the vaccine. CIP/SIP system 1032 maintains the sterility of the system.

The plug-and-play modules for manufacturing a yellow fever vaccine preferably include seeds 1040, inoculation robotic arm 1042, seed fermenter 1047, fermenter 1048, Microfiltration system 1036, cell DNA digestion system 1034, ultra-filtration system 1035, and chromatography system 1024. The supervisory control 1028 preferably controls the flow of material through the modules to manufacture the yellow fever vaccine 1060. As shown in the figure, ultra-filtration may occur multiple times during the process.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the following claims. Furthermore, the term "comprising of" includes the terms "consisting of" and "consisting essentially of."

The invention claimed is:

1. A modular system for just-in-time manufacturing of a plurality of biologicals, comprising:
 a supervisory control system, wherein the supervisory control system executes software adapted to manufacture a desired biological;
 a batch manufacturing records database in communication with the supervisory control system, wherein the batch manufacturing records database stores a plurality of instructions for manufacturing different biologicals;
 an automatic clean in place and sterilize in place system adapted to maintain the sterility of the system; and
 a plurality of different of plug-in-play manufacturing modules, wherein at least one of the plurality of different plug-in-play manufacturing modules is coupled to the system based on the desired biological;
 wherein the supervisory control system obtains instructions for manufacturing the desired biological from the batch manufacturing records database, determines what plug-in-play manufacturing modules are coupled to the system, and controls flow of matter through each of the plug-in-play manufacturing modules coupled to the system based on the instructions for manufacturing the desired biological.

2. The system of claim 1, wherein the biologicals are one of cells, viruses, bacteria, bacterial products, recombinant products, and vectored products.

3. The system of claim 2, wherein the vaccines are one of polysaccharide vaccines, inactivated whole-cell pertussis vaccines, cell based inactivated influenza vaccines, inactivated rabies vaccines, hepatitis vaccines, and yellow fever live-attenuated vaccines.

4. The system of claim 1, wherein the plug-in-play manufacturing modules are chosen from the group comprising scale-up fermentation modules, centrifugation modules, chromatography modules, homogenization modules, enzyme reaction modules, acid digestion modules, inactivation modules, alkaline digestion modules, diafiltration modules, cross flow filtration modules, ultrafiltration modules, microfiltration modules, and inoculation modules.

5. The system of claim 4, wherein the inoculation modules include at least one of isolated seed vials, cold-storage, a robotic arm, a seed fermenter, a one-way sterile material transfer system, a full scale fermenter, and an isolation system.

6. The system of claim 1, wherein the system is mobile and adapted to be setup on site.

7. The system of claim 1, wherein the biological is manufactured in less than 5 weeks.

8. The system of claim 1, wherein the system is autonomous.

9. The system of claim 1, wherein the system is a closed system.

10. The system of claim 1, wherein the system is scalable to increase output.

11. The system of claim 1, further comprising software adapted to record manufacturing records.

12. The system of claim 1, further comprising an alert system adapted to indicate breakdowns in the process and transmit instructions to correct the breakdowns.

13. The system of claim 1, wherein the supervisory control system validates the produced biologicals.

14. The system of claim 13, wherein the validation is tamper-proof.

15. The system of claim 1, wherein the system manufacturers biologicals continuously.

16. The system of claim 13, wherein the validations is a quality control validation.

* * * * *